US006270511B1

(12) United States Patent
Markman

(10) Patent No.: US 6,270,511 B1
(45) Date of Patent: *Aug. 7, 2001

(54) HAIR TRANSPLANT IMPLANTER AND TEMPLATE SYSTEM

(76) Inventor: Barry S. Markman, 5157 Jarom, Las Vegas, NV (US) 89120

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/095,851

(22) Filed: Jun. 10, 1998

Related U.S. Application Data

(63) Continuation-in-part of application No. 08/873,852, filed on Jun. 14, 1997, now Pat. No. 5,868,758, which is a continuation-in-part of application No. 08/561,018, filed on Nov. 21, 1995, now Pat. No. 5,792,169, which is a continuation-in-part of application No. 08/395,455, filed on Feb. 28, 1995, now Pat. No. 5,643,308.

(51) Int. Cl.$^7$ ............................................. A61B 17/00
(52) U.S. Cl. .............................................................. 606/187
(58) Field of Search ............................. 606/187; 428/131, 428/132

(56) References Cited

U.S. PATENT DOCUMENTS

| 269,039 | * | 12/1882 | French | 428/131 |
| 1,411,973 | * | 4/1922 | Mahoney | 428/131 |
| 1,542,427 | * | 6/1925 | Wardell | 428/132 |
| 3,831,202 | * | 8/1974 | Hulsen | 606/187 |
| 4,731,279 | * | 3/1988 | Isshiki | 428/159 |
| 5,500,270 | * | 3/1996 | Langdon et al. | 428/119 |
| 5,643,308 | * | 7/1997 | Markman | 606/187 |

* cited by examiner

*Primary Examiner*—Michael H. Thaler
(74) *Attorney, Agent, or Firm*—Milbank, Tweed, Hadley & McCloy LLP

(57) ABSTRACT

A system for use in implanting hair grafts in tissue and for preventing the corruption of implanted hair grafts during the implantation of further hair grafts is provided. The system includes a hair graft implanter and a template. The template has a body with an upper and lower surface and a plurality of openings therethrough each adapted to pass a transplantation catheter for implantation of a graft into the tissue. Projections or flat areas are provided on the bottom surface of the body to rest upon and cover previously transplanted grafts to hold them in position, support the tissue and thereby resist corruption thereof by the implanter's subsequent incising, dilation and transplantations of grafts through the template.

15 Claims, 1 Drawing Sheet

HAIR TRANSPLANT IMPLANTER AND TEMPLATE SYSTEM

CROSS REFERENCE TO RELATED APPLICATIONS

This application is a continuation-in-part of application U.S. Ser. No. 08/873,852, filed Jun. 14, 1997, now U.S. Pat. No. 5,868,758, which is in turn a continuation-in-part of application U.S. Ser. No. 08/561,018 filed Nov. 21, 1995, now U.S. Pat. No. 5,792,169, which is a continuation-in-part of application U.S. Ser. No. 08/395,455 filed Feb. 28, 1995, now U.S. Pat. No. 5,643,308, which are incorporated herein by this reference.

FIELD OF THE INVENTION

The present invention relates to devices for transplantation of hair grafts. More particularly, the present invention relates to a template adapted to minimize corruption of graft sites during transplantation.

BACKGROUND OF THE INVENTION

In transplantation of hair grafts, as is presently known, live hair grafts are cultivated from a region such as at the hair line at the back of the neck and are transplanted where desired at locations on the scalp. To provide a natural look in locations on the scalp, it is desired to place grafts in closely adjacent sites in a pre-determined pattern. Because of the close proximity of the sites, several sessions may be required. For example, one session may place some grafts and then several weeks later, after the previous grafts and the incisions to receive the same have healed, a second session places grafts between those previously positioned. Corruption may occur when the incision is made to receive a graft with the incision encroaching upon a previously positioned graft. If a graft has been placed and the incision for the next adjacent site is too near, the incisions may invade and corrupt the tissues supporting the previous graft damaging the graft, disturbing the graft pattern, delaying healing or increasing the risk of infection. Hence, multiple sessions are typically required.

To implant grafts, it is known to incise the tissue and to individually position grafts in the incisions. Additionally, I have invented a system which incises and dilates the tissue with a catheter and thereafter moves the graft through the catheter into the graft site as disclosed in U.S. Pat. No. 5,643,308. Where a singular catheter or tube or multiple catheter/incisions are used, it may be necessary to make multiple "strikes" to incise, dilate and transplant grafts f or closely adjacent sites to obtain the desired transplantation pattern. The closeness of the sites presents a challenge to avoid corruption of the previously placed grafts.

Accordingly, there is a need for a device which can protect previously placed grafts from corruption when closely adjacent grafts are placed.

Further, there is a need for the device which can assist in obtaining the desired graft patterns and which provides the desired protective effect.

SUMMARY OF THE INVENTION

There is, therefore, set forth according to the present invention a template for use in placing hair grafts in tissue. The template has a body with an upper and lower surface and a plurality of openings therethrough each adapted to pass a transplantation catheter for implantation of a graft into the tissue. Projections are provided on the bottom surface of the body to rest upon and cover previously transplanted grafts to hold them in position, support the tissue and thereby resist corruption thereof by the subsequent incising, dilation and transplantations of grafts through the template.

In a specific embodiment, a template for use in transplanting hair grafts at pre-determined pattern of N graft sites arranged in a pre-determined pattern using a catheter to dilate and guide a graft into the site comprises a planar body having an upper and lower surface and N/2 openings therethrough to pass the catheter for placement of the grafts into the tissue. A plurality of projections are disposed on a lower surface between the openings, the projections adapted to press down upon previously placed grafts to hold them in position and support the tissue. The projections are disposed such that a first set of grafts are transplanted through the openings defined by the template into graft sites and the body is moved or indexed such that the projections cover the first transplant set and the openings are disposed for transplantation of a next set of grafts in locations between the sites defined by the first set of grafts.

The template not only provides a pattern guide for the placement of the grafts but covers, holds and supports the previously placed grafts so that incising, dilating and placement of the next adjacent graft is less likely to corrupt the first set of grafts.

BRIEF DESCRIPTION OF THE DRAWINGS

These and other features and advantages will become appreciated as the same becomes better understood with reference to the specification, claims and drawings wherein:

DESCRIPTION

Figure 1:
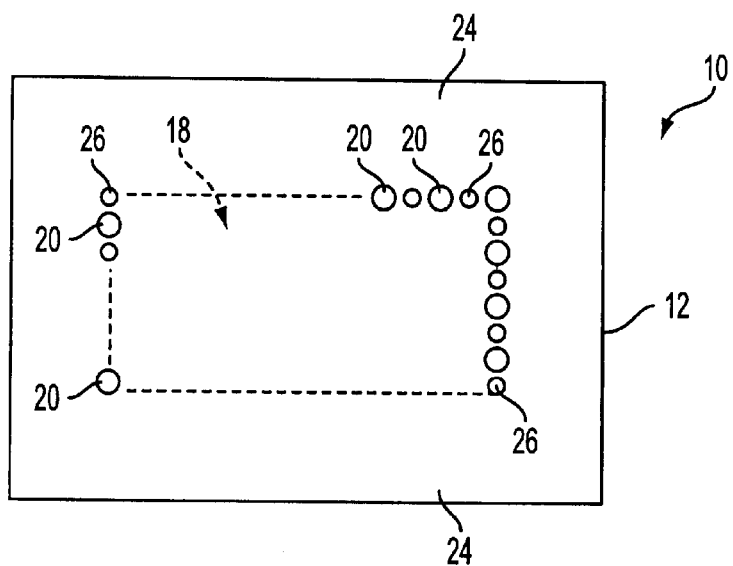
FIG. 1 is a bottom view of the template according to the present invention.
Figure 2:
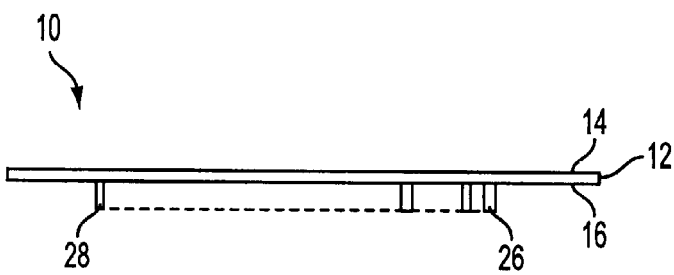
FIG. 2 is a side view of the template according to the present invention.

Turning to FIGS. 1 and 2, a template 10 according to the present invention is shown. The template 10 has a planar body 12 with upper and lower surfaces 14, 16. The body 12 is provided with a pattern 18 of openings 20 each adapted to pass a hair graft 27 in a manner described below. The pattern 18 is preferably centrally located on the body 12 to provide a margin 24 for grasping, holding and positioning during the transplantation process. The body 12 may be fashioned from a suitable plastic material and may be rigid or somewhat flexible. Furthermore, the body 12, instead of provided with the openings 20, may be fashioned from a rubberized material with the openings 20 scored or provided by frangible portions piercable by the incising device as hereinafter described. The body 12 may have a thickness of approximately 0.028 to 0.032 inches.

Disposed at the lower surface 16 are a plurality of depending projections 26 each adapted in the manner described below to support a graft and the surrounding tissue in a manner to resist corruption. Each of the projections 26 may be cylindrical fashioned from substantially rigid materials such as plastic and have a flat end 28. Each projection may have a diameter of approximately 0.030 inches and may extend approximately 0.048 inches.

Figure 3:
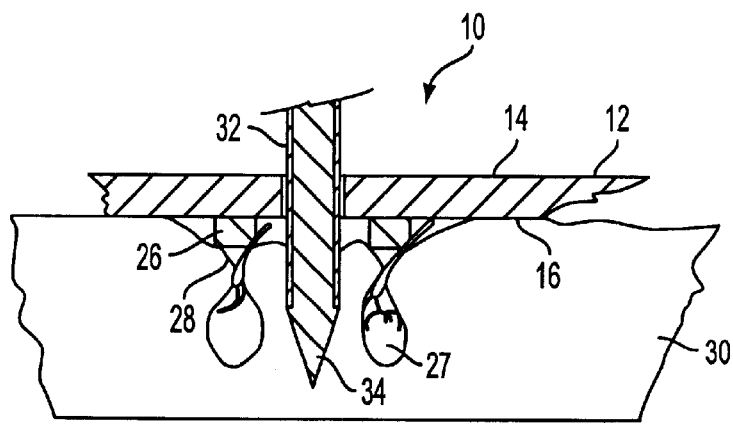
FIG. 3 is a side section view of the template in use with a catheter/incisor for placing of hair grafts.

As shown in FIG. 1, the pattern 18 of the openings 20 may be placed in a series of rows or columns defining a matrix of openings 20 spaced apart by the projections 26. Each opening 20 may have a diameter of approximately 0.090 inches. According to this pattern, and where the openings 20 are spaced apart a distance D, the desired pattern of grafts will be placed apart by a distance of D/2. With reference to FIG. 3, the operation of the template 10 will now be described.

In use, the surgeon places the template 10 against the tissue 30 after the same has been prepared and inflated with a saline solution. Using the pattern 18 of the openings 20, the surgeon incises the tissue by passing a catheter 32 containing an incising needle 34 therethrough to puncture the tissue 30 as suggested in FIG. 3. Thereafter, the needle 34 is withdrawn from the catheter 32, the catheter 32 dilating the tissue 30. A graft 27 previously cultivated is moved through the catheter 32 into the graft site. After the surgeon has placed all the grafts 27 as defined by the pattern 18 of openings 20, the surgeon moves the templates 10 such that the projections 26, and more particularly their ends 28, press against the previously transplanted grafts 27 to support them as transplanted as well as the surrounding tissue 30. In this position, the openings 20 have been located in a position between the previously placed grafts 27. The surgeon, in the manner described above, thereafter transplants grafts in the interstices of the previously placed set of grafts 27 by incising and dilating the tissue as shown in FIG. 3. While incising and dilating the tissue 30, the projections 26 support the previously placed grafts 27 to resist corruption of the tissue during transplantation of the next set of grafts 27.

The arrangement of the openings 20 and projections 26 of the pattern 18 provide for this indexing of the template described above to cover the first set of grafts 27 and register the openings 20 for placement of the second set of grafts in spaces between the grafts of the first set.

While I have shown and described certain embodiments of the present invention, it is to be understood that it is subject to many modifications and changes without departing from the spirit and scope of the appended claims.

I claim:

1. A system for use in placing additional hair grafts in tissue having hair grafts previously transplanted in a predetermined spacing comprising:
    a device for implanting at least one hair graft into the scalp of a patient, including a base; at least one guide extending downwardly from said base, said guide having a guide passage therethrough; a depressor movable with respect to said guide and said base, and at least one spike extending downwardly from said depressor, said spike movable within said guide passage, whereby said spike is movable to a spike position where said spike and said guide cooperate to dilate a cavity in the scalp, and said spike is movable to engage the hair graft and push the hair graft through said guide into said cavity; and
    a template including a body having a top surface and a bottom surface; projections having a predetermined spacing disposed on said bottom surface, said projections being substantially non-hollow and having surfaces for substantially resting upon and covering the previously transplanted hair grafts and for substantially resisting corruption thereof by the additional hair grafts and said guide passed through said body into the tissue; and a plurality of openings through said body for passing the additional hair grafts and said guide through said body into the tissue, said openings having a predetermined spacing, each of said openings offset from said projections.

2. The system of claim 1 wherein a predetermined pattern of said openings and a predetermined pattern of said projections correspond to a predetermined pattern of the previously transplanted hair grafts.

3. The system of claim 1 wherein said body is approximately 0.028 to 0.032 inches in thickness and said projections extend approximately 0.048 inches.

4. The system of claim 1 wherein said openings have a diameter of approximately 0.090 inches.

5. The system of claim 1 wherein said projections have a diameter of approximately 0.030 inches.

6. The system of claim 1 wherein a total number of graft sites is approximately twice the number of said openings and is approximately twice the number of said projections.

7. A system for use in increasing the density of hair grafts transplanted into tissue, for transplanting hair grafts in a predetermined spaced pattern of a predetermined number of hair graft sites arranged in adjacent rows, for transplanting first hair grafts and for substantially resisting corruption of previously transplanted second hair grafts, said first and second hair grafts placed using a device for implanting hair grafts, said second hair grafts transplanted in a strike pattern corresponding to at least a portion of said hair graft pattern, comprising:
    a device for implanting at least one hair graft into the scalp of a patient, including a base; at least one guide extending downwardly from said base, said guide having a guide passage therethrough; a depressor movable with respect to said guide and said base; and at least one spike extending downwardly from said depressor, said spike movable within said guide passage, whereby said spike is movable to a spike position where said spike and said guide cooperate to dilate a cavity in the scalp, and said spike is movable to engage the hair graft and push the hair graft through said guide into said cavity; and
    a template including a planar body having an upper and a lower surface and having approximately one-half said predetermined number of openings therethrough to pass said guide for placement of a hair graft into the tissue; and a plurality of projections disposed on said lower surface between and offset from said openings, said projections being substantially non-hollow and having surfaces disposed for substantially covering the second hair grafts and having surfaces said openings are disposed for transplanting the first hair grafts between the second hair grafts.

8. The system of claim 7 wherein said hair graft pattern consists of hair graft sites located on a first grid having predetermined lateral and longitudinal spacings and on a second grid having said predetermined lateral and longitudinal spacings, said second grid offset from said first grid by approximately one-half said lateral spacing and approximately one-half said longitudinal spacing, the strike pattern corresponding to said second grid, said openings disposed to pass hair grafts into the tissue into hair graft sites located on said first grid and said projections offset from said openings such that said projections are disposed to substantially cover hair graft sites located on said second grid.

9. The system of claim 7 wherein said body is approximately 0.028 to 0.032 inches in thickness and said projections extend approximately 0.048 inches.

10. The system of claim 7 wherein said projections have a diameter of approximately 0.090 inches.

11. The system of claim 7 wherein said projections have a diameter of approximately 0.030 inches.

12. The system of claim 2 wherein the predetermined pattern is a rectangular grid having lateral and longitudinal spacings, and said openings are offset from said projections by a lateral distance of approximately one-half said lateral spacing and by a longitudinal distance of approximately one-half said longitudinal spacing.

13. A system for use in placing additional hair grafts in tissue having hair grafts previously transplanted in a predetermined spacing comprising:

a device for implanting at least one hair graft into the scalp of a patient, including a base; at least one guide extending downwardly from said base, said guide having a guide passage therethrough; a depressor movable with respect to said guide and said base; and at least one spike extending downwardly from said depressor, said spike movable within said guide passage, whereby said spike is movable to a spike position where said spike and said guide cooperate to dilate a cavity in the scalp, and said spike is movable to engage the hair graft and push the hair graft through said guide into said cavity; and a template including a body having a top surface and a bottom surface, said bottom surface including substantially flat areas, said flat areas having the predetermined spacing for substantially resting upon and covering the previously transplanted hair grafts and for substantially resisting corruption thereof by the additional hair grafts passed through said guide and said body into the tissue; and a plurality of openings through said body for passing the additional hair grafts and said guide through said body into the tissue, said openings having the predetermined spacing, each of said openings offset from said flat areas.

14. The system of claim 13 wherein said flat areas have a diameter of approximately 0.030 inches.

15. The system of claim 13 wherein the predetermined pattern is a rectangular grid having lateral and longitudinal spacings, and said openings are offset from said projections by a lateral distance of approximately one-half said lateral spacing and by a longitudinal distance of approximately one-half said longitudinal spacing.

* * * * *